United States Patent [19]

Davies et al.

[11] Patent Number: 4,710,506

[45] Date of Patent: Dec. 1, 1987

[54] ANTIHYPERTENSIVE THIENOPYRIDINES

[75] Inventors: Roy V. Davies, Nottinghamshire; James Fraser, Nottingham, both of England

[73] Assignee: The Boots Company PLC, England

[21] Appl. No.: 874,337

[22] Filed: Jun. 13, 1986

[30] Foreign Application Priority Data

Jun. 15, 1985 [GB] United Kingdom ............... 8515207

[51] Int. Cl.[4] ..................... A61K 31/44; C07D 495/04
[52] U.S. Cl. .................................... 514/301; 546/114
[58] Field of Search ........................ 546/114; 514/301

[56] References Cited

U.S. PATENT DOCUMENTS 3,997,545 12/1976 Kuwada et al. ................. 546/114
4,302,460 11/1981 Davies et al. ................... 546/155
4,447,435  5/1984 Davies ............................ 546/153

FOREIGN PATENT DOCUMENTS 0046990 8/1981 European Pat. Off. .
0157324 4/1985 European Pat. Off. .

Primary Examiner—Henry R. Jiles
Assistant Examiner—Bernard I. Dentz
Attorney, Agent, or Firm—Jacobs & Jacobs

[57] ABSTRACT

Novel thienopyridones with antihypertensive activity have the formula I,

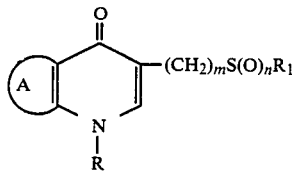

wherein the ring A represents an optionally substituted thiophene ring; m is 0 or 1; n is 0, 1 or 2; R is lower alkyl and $R_1$ is lower alkyl.

The fused thieno-ring may carry one or two substituents.

Formula I encompasses thieno[3,2-b]pyridones, thieno[3,4-b]pyridones and thieno[2,3-b]pyridones.

Processes for preparing the novel thienopyridones and pharmaceutical compositions containing them are described. Pharmaceutically acceptable acid addition salts of the compounds of formula I are also described.

The thienopyridones of formula I are antihypertensive agents and are also indicated for use in treating heart failure and ischaemic heart disease.

36 Claims, No Drawings

ANTIHYPERTENSIVE THIENOPYRIDINES

This invention relates to novel thienopyridones with therapeutic activity as antihypertensive agents, to therapeutic compositions containing the thienopyridones and to processes for preparing the thienopyridones.

The present invention provides novel thienopyridones of formula I,

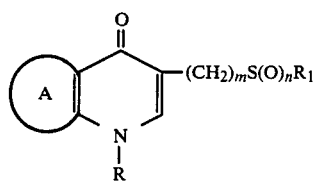

and, pharmaceutically acceptable acid addition salts thereof, wherein the ring A represents an optionally substituted thiophene ring; m is 0 or 1; n is 0, 1 or 2; R is lower alkyl and $R_1$ is lower alkyl.

The fused thieno-ring may carry one or two substituents.

It will be appreciated by those skilled in the art that formula I encompasses thieno[3,2-b]pyridones of formula II, thieno[3,4-b]pyridones of formula III and thieno[2,3-b]pyridones of formula IV,

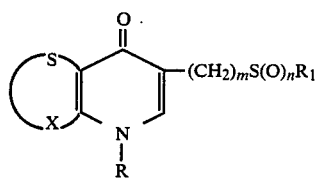

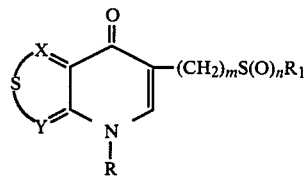

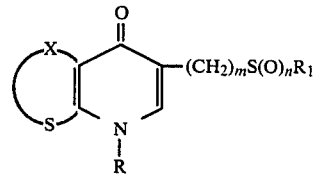

wherein X or X and Y together represent the residue of an optionally substituted thiophene ring and m, n, R and $R_1$ are as hereinbefore defined. In general, the compounds of formula II are the preferred compounds of the present invention. Of the remaining compounds, the compounds of formula III are preferred to the compounds of formula IV. More particular compounds of formulae I to IV are those in which the thiophene ring optionally contains one or two substituents selected from lower alkyl; lower alkoxy; lower alkylthio; lower alkylsulphinyl; lower alkylsulphonyl; halo; cyano; fluorinated lower alkyl; fluorinated lower alkoxy; the group Ar, ArO, ArS, ArSO or $ArSO_2$ wherein Ar is phenyl optionally substituted by 1 to 4, especially 1 or 2, groups selected from lower alkyl, lower alkoxy, lower alkylthio, halo and trifluoromethyl. Preferably the thiophene ring is unsubstituted or contains one substituent.

The term "lower" signifies a group with 1 to 4 carbon atoms. Any alkyl chain in the above-mentioned groups may be straight or branched and may be, for example, methyl, ethyl, n- or iso-propyl, n-, sec-, iso- or tert-butyl. The term "halo" preferably signifies fluoro, chloro or bromo. A preferred fluorinated lower alkyl group is trifluoromethyl. Preferred fluorinated lower alkoxy groups are difluoromethoxy and 2,2,2-trifluoroethoxy.

More preferred substituents in the thiophene ring of the formulae I to IV are lower alkyl; lower alkoxy; halo; and phenyl; phenyl substituted by 1 to 3, especially 1 or 2, groups selected from lower alkyl, lower alkoxy and halo. Preferably the thiophene ring is unsubstituted or contains one such substituent.

Particular values of these more preferred substituents include, for example, methyl, ethyl, methoxy, ethoxy, phenyl, 2-chlorophenyl and 3-chlorophenyl.

An especially preferred group of compounds of the present invention is that of the formula V,

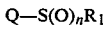   V wherein n is 0 or 1, $R_1$ is lower alkyl, and Q is a group of the formula VA or VB,

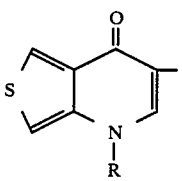   VA

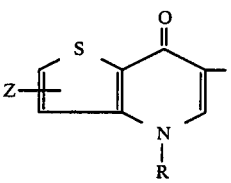   VB wherein R is lower alkyl and Z in formula VB is hydrogen, lower alkoxy, 2-(lower alkyl), 2-phenyl, 2-(2-halophenyl) or 2-(3-halophenyl). R and $R_1$ are preferably methyl. Preferably Q is the group of formula VB.

Particular values of Z are, for example, hydrogen, methoxy, ethoxy, 2-methyl, 2-phenyl, 2-(2-chlorophenyl) and 2-(3-chlorophenyl).

Another especially preferred group of compounds of the present invention is that of the formula VC,

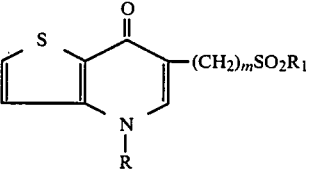   VC wherein m is 0 or 1, R is lower alkyl and $R_1$ is lower alkyl. Preferably R and $R_1$ are methyl.

Preferred compounds of this invention include the following:

A: 4-methyl-6-methylsulphinylthieno[3,2-b]pyrid-7(4H)-one;

B: 4-methyl-6-methylsulphonylthieno[3,2-b]pyrid-7(4H)-one;
C: 4-methyl-6-methylsulphonylmethylthieno[3,2-b]pyrid-7(4H)-one;
D: 4-methyl-6-methylsulphinyl-2-phenylthieno[3,2-b]pyrid-7(4H)-one;
E: 3-ethoxy-4-methyl-6-methylsulphinylthieno[3,2-b]pyrid-7(4H)-one;
F: 2-(2-chlorophenyl)-4-methyl-6-methylsulphinylthieno[3,2-b]pyrid-7(4H)-one;
G: 2-(2-chlorophenyl)-4-methyl-6-methylthiothieno[3,2-b]pyrid-7(4H)-one.

Compound A is an especially preferred compound.

It will be appreciated by those skilled in the art that, in the compounds of the hereinbefore defined formula I wherein n is 1, the group $R_1SO$ contains a chiral centre at the sulphur atom. Thus such compounds exist in two enantiomeric forms. The present invention includes both enantiomers and mixtures thereof.

We have found that the compounds of formula I have antihypertensive activity. The compounds reduce blood pressure when administered to hypertensive mammals.

The compounds of formula I form acid addition salts with inorganic or organic acids, for example hydrochloric acid, fumaric acid, tartaric acid and citric acid. It will be appreciated that such salts, provided they are pharmaceutically acceptable, may be used in therapy in place of the corresponding compounds of formula I. Such salts are prepared by reacting the compound of formula I with a suitable acid in a conventional manner.

The present invention provides pharmaceutical compositions which comprise a compound of formula I or a pharmaceutically acceptable acid addition salt thereof together with a pharmaceutically acceptable carrier.

As used hereinafter, the term "active compound" denotes a thienopyridone of general formula I, or a pharmaceutically acceptable acid addition salt thereof. In therapeutic use, the active compound may be administered orally, rectally, parenterally or topically, preferably orally. Thus the therapeutic compositions of the present invention may take the form of any of the known pharmaceutical compositions for oral, rectal, parenteral or topical administration. Pharmaceutically acceptable carriers suitable for use in such compositions are well known in the art of pharmacy. The compositions of the invention suitably contain 0.1–90% by weight of active compound. The compositions of the invention are generally prepared in unit dosage form.

Compositions for oral administration are the preferred compositions of the invention and these are the known pharmaceutical forms for such administration, for example tablets, capsules, syrups and aqueous or oily suspensions. The excipients used in the preparation of these compositions are the excipients known in the pharmacist's art. Tablets may be prepared by mixing the active compound with an inert diluent such as calcium phosphate in the presence of disintegrating agents, for example maize starch, and lubricating agents, for example magnesium stearate, and tableting the mixture by known methods. Such tablets may, if desired, be provided with enteric coatings by known methods, for example by the use of cellulose acetate phthalate. Similarly capsules, for example hard or soft gelatin capsules, containing the active compound with or without added excipients, may be prepared by conventional means and, if desired, provided with enteric coatings in a known manner. Enteric coated compositions of the invention may be advantageous, depending on the nature of the active compound. The tablets and capsules may conveniently each contain 1–500 mg of the active compound. Other compositions for oral administration include, for example, aqueous suspensions containing the active compound in an aqueous medium in the presence of a non-toxic suspending agent such as sodium carboxymethylcellulose, and oily suspensions containing a compound of the present invention in a suitable vegetable oil, for example arachis oil.

Compositions of the invention suitable for rectal administration are the known pharmaceutical forms for such administration, for example, suppositories with cocoa butter or polyethylene glycol bases.

Compositions of the invention suitable for parenteral administration are the known pharmaceutical forms for such administration, for example, sterile suspension in aqueous and oily media or sterile solutions in a suitable solvent.

Compositions for topical administration may comprise a matrix in which the active compound is dispersed so that the compound is held in contact with the skin in order to administer the active compound transdermally. Alternatively the active compound may be dispersed in a cream or ointment base.

In some formulations it may be beneficial to use the compounds of the present invention in the form of particles of very small size, for example, as obtained by fluid energy milling.

In the compositions of the present invention the active compound may, if desired, be associated with other compatible pharmacologically active ingredients, for example a β-blocker such as propranolol, oxprenolol or timolol, or a diuretic such as bendrofluazide.

The therapeutic activity of the compounds of general formula I has been demonstrated by means of tests on standard laboratory animals. Such tests include, for example, the oral administration of the compounds to a strain of spontaneously hypertensive rat and the intraduodenal administration of compounds to a strain of normotensive rat. Thus the compounds of formula I are useful for reducing blood pressure in hypertensive mammals including humans. A suitable dose for enteral administration to mammals, including humans, is generally within the range 0.1–25 mg/kg/day, more usually 0.5–10 mg/kg/day, given in single or divided doses. For parenteral administration, a suitable dose is generally within the range 0.01–2.5 mg/kg/day, especially 0.05–1.0 mg/kg/day. Oral administration is preferred.

We have found that the compounds of formula I are vasodilators with a dilating action on both arteriolar and venous vascular beds. Accordingly the compounds are indicated for use in the treatment of ischaemic heart disease and heart failure in mammals, including humans. Suitable dosages are those given above.

The compounds of formula I may be prepared by alkylation of a compound of formula VI,

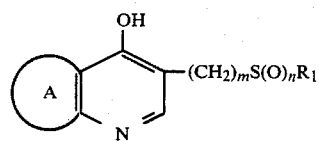

VI wherein the ring A, $R_1$, m and n are as hereinbefore defined. The alkylation may be effected by reacting the compound of formula VI with an alkylating agent, e.g.

a dialkyl sulphate or an alkyl halide such as an alkyl iodide, in a conventional manner for such reactions.

The intermediates of formula VI are novel. The intermediates of formula VI wherein m is 0 and n is 0 may be prepared by cyclisation of a compound of formula VII,

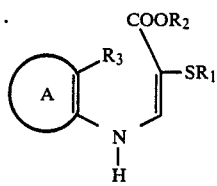   VII wherein $R_2$ is lower alkyl, preferably methyl or ethyl and $R_3$ is hydrogen or carboxy.

Depending upon the position of the sulphur atom in ring A and, in some instances, the reaction conditions, this cyclisation gives a thieno[3,2-b]pyridine, a thieno[3,4-b]pyridine or a thieno[2,3-b]pyridine within formula VI wherein m is 0 and n is 0.

For example, cyclisation of a compound of formula VIIA,

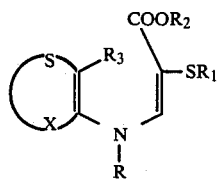   VIIA by heating the compound at a temperature within the range 200° to 280°, for example by boiling a mixture of the compound and diphenyl ether under reflux, gives the thieno[3,2-b]pyridines of formula VIA,

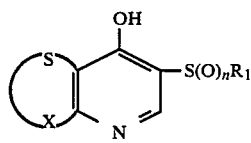   VIA wherein n is 0.

As another example, cyclisation of a compound of formula VIIA wherein $R_3$ is carboxy by heating the compound with polyphosphate ester at a temperature within the range 60° to 140°, gives the thieno[3,4-b]pyridines of formula VIB,

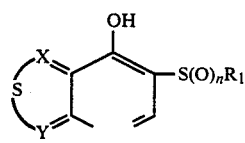   VIB wherein n is 0.

As a further example, cyclisation of a compound of formula VIIC,

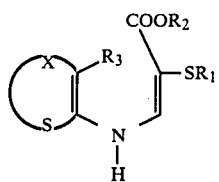   VIIC for example by heating the compound at a temperature in the range 200° to 280°, for example by boiling a mixture of the compound and diphenyl ether under reflux, gives the thieno[2,3-b]pyridines of formula VIC,

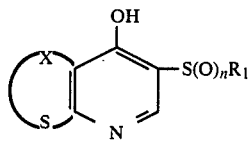   VIC wherein n is 0.

The compounds of formulae VI, VIA, VIB and VIC wherein n is 1 may be prepared by oxidation of the corresponding compounds wherein n is 0. Similarly the compounds of formulae VI, VIA, VIB and VIC wherein n is 2 may be prepared by oxidation of the corresponding compounds wherein n is 0 or 1. A suitable oxidising agent is, for example, an organic peracid such as 3-chloroperbenzoic acid.

The intermediates of formula VII, which encompasses formulae VIIA and VIIC, are novel compounds.

The compounds of formula VII may be prepared by reacting a compound of formula VIII,

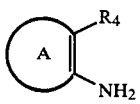   VIII wherein $R_4$ is hydrogen or COOM and M is an alkali metal, for example sodium, with an acrylate of formula IX,

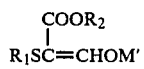   IX wherein M' is an alkali metal, for example sodium.

The acrylates of formula IX may be prepared for example by reacting a compound of formula X,

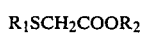   X with sodium methoxide to give the corresponding anion, sodium salt, which is then reacted with methyl formate.

The compounds of formula VI wherein m is 1 and n is 0 may be prepared by reaction of a compound of formula XI,

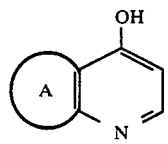   XI with formaldehyde and the appropriate alkanethiol. Paraformaldehyde may be used as a convenient source of formaldehyde. The compounds of formula VI wherein m is 1 and n is 1 may be prepared by the oxidation of the corresponding compounds wherein n is 0. Similarly the compounds of formula VI wherein m is 1 and n is 2 may be prepared by oxidation of the corresponding compounds wherein n is 0 or 1. A suitable oxidising agent is, for example, an organic peracid such as 3-chloroperbenzoic acid. The corresponding compounds wherein n is 2 may also be prepared by reaction of the compound of formula XI with formaldehyde and the appropriate alkali metal alkanesulphinate, for example sodium methanesulphinate.

The compounds of formula XI may be prepared by hydrolysis followed by decarboxylation of a compound of formula XII,

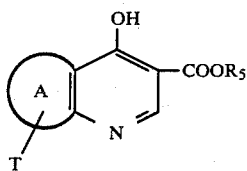

XII wherein $R_5$ is lower alkyl, preferably methyl or ethyl and T is hydrogen or $COOR_6$ and $R_6$ is lower alkyl.

The compounds of formula I in which m is 0 may be prepared by reacting a compound of formula XIII,

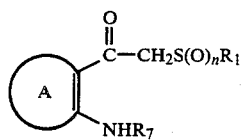

XIII wherein $R_7$ is R with a tri(lower alkyl) orthoformate, especially trimethyl orthoformate or triethyl orthoformate. When $R_7$ is hydrogen, this reaction gives the compounds of formula VI wherein m is 0.

The compounds of formula XIII may be prepared by reacting a compound of formula XIV wherein $R_8$ is lower alkyl, preferably methyl or ethyl,

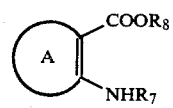

XIV with a compound of formula XV,

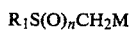

XV wherein M is an alkali metal, for example sodium.

The intermediates of formula XIII are novel.

The compounds of formula I in which m is 1 and n is 0 or 2 may be prepared by reacting a compound of formula XVI,

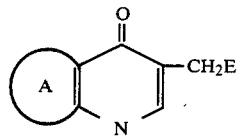

XVI wherein E is a suitable leaving group, for example, halo such as chloro or alkanoyloxy such as acetoxy, with a compound of formula XVII,

XVII wherein n is 0 or 2 and M is an alkali metal, for example sodium.

The compounds of formula XVI may be prepared in the following way. A compound of formula XI is reacted with formaldehyde to give a compound of formula XIA,

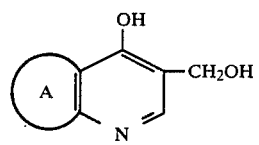

XIA

The compound of formula XIA is alkylated to give the corresponding N-alkylthienopyridone compound and the hydroxymethyl group in this compound is then converted to the appropriate group —$CH_2E$ by known methods. For example, reaction with thionyl chloride gives the compounds wherein E is chloro.

The intermediates of formula XVI are novel.

The compounds of formula I which contain a replaceable halo substituent in the thiophene ring may be used to prepare the corresponding compounds wherein the halo substituent is replaced by another substituent. For example, reaction with lower alkoxide ion, lower alkylthiolate ion, fluorinated lower alkoxide ion, phenoxide ion, phenylthiolate ion, lower alkanesulphonate ion or phenylsulphonate ion gives the corresponding compounds wherein halo is replaced by lower alkoxy, lower alkylthio, fluorinated lower alkoxy, phenoxy, phenylthio, lower alkylsulphonyl or phenylsulphonyl.

The compounds of formula I wherein n is 1 may be prepared by oxidation of the corresponding compounds wherein n is 0. Similarly the compounds of formula I wherein n is 2 may be prepared by oxidation of the corresponding compounds wherein n is 0 or 1. Suitable oxidising agents include organic peracids such as 3-chloroperbenzoic acid.

It will be appreciated by those skilled in the art that the moiety of formula XVIII,

XVIII which occurs in many of the hereinbefore described formulae, encompasses the moieties of the formulae XVIIIA, XVIIIB and XVIIIC,

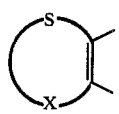

XVIIIA

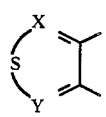

XVIIIB

-continued

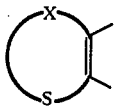   XVIIIC wherein X and Y are as hereinbefore defined.

Certain compounds of the invention may exist in more than one polymorphic form. For example, 4-methyl-6-methylsulphinylthieno[3,2-b]pyrid-7(4H)-one can exist in at least two polymorphic forms, designated "Type 1" and "Type 2", which have characteristic infra-red spectra and different melting points. Type 2 is metastable with respect to Type 1 and converts to Type 1 on heating, on grinding or during periods of storage.

As mentioned above, the therapeutic acitvity of the quinolones of the present invention has been demonstrated by tests which include (A) the oral administration of the compounds to a strain of spontaneously hypertensive rat and (B) the intraduodenal administration of the compounds to a strain of normotensive rat. These tests were carried out in the following way:

TEST A

Female rats, weight range 180–240 g, of the Aoki-Okamoto strain of spontaneously hypertensive rat were used. The rats in groups of four were fasted overnight before administration of the test compound. Blood pressure was determined in the following way. The rats were placed in a cabinet kept at 38° C. with their tails protruding through holes in the cabinet. After 30 minutes in the cabinet blood pressure was measured using an inflatable cuff placed round the base of the tail and arterial pulsations monitored with a pneumatic pulse transducer. A pressure, greater than the expected blood pressure, was applied to the cuff, and this pressure was slowly reduced. The pressure in the cuff at which arterial pulsations reappeared was taken as the blood pressure. The rats were removed from the cabinet and each group orally dosed with a given dose of the test compound given as a solution or suspension in 0.25% aqueous carboxymethylcellulose. In addition to the pre-dose reading, blood pressure was measured at 1.5 and 5.0 hours after dosing. A compound was designated as active if it gave a reduction of blood pressure equal to or greater than that considered to be the minimum significant reduction ($p < 0.01$) on the basis of historical control data.

TEST B

Male normotensive rats (Wistar strain) of weight range 210–240 g were used. The rats were anaesthetised and cannulae placed in a carotid artery and in the duodenum. Blood pressure was recorded electronically by means of a pressure transducer connected to the arterial cannula. The test compound was administered into the duodenum as a solution or suspension in 0.25% aqueous carboxymethylcellulose. Blood pressure was recorded before dosing and for 30 minutes afterwards. Results were obtained as the mean of determinations in three rats per dosage level. Compounds which caused an obvious drug-related fall in blood pressure of 14% or greater during the 30 minute post-dose period were designated as active.

The final products of Examples 1–28 were active in one or both of Tests A and B at a dosage of 90 mg/kg or less.

The invention is illustrated by the following non-limitative Examples, in which parts and percentages are by weight and compositions of mixed solvents are given by volume. Novel compounds were characterised by one or more of the following spectroscopic techniques: nuclear magnetic resonance, infra-red and mass spectroscopy. Temperatures are given in degrees Celsius.

EXAMPLE 1

(a) Sodium (6.9 g) was dissolved in dry methanol (200 ml) and the solution evaporated to dryness. The resulting sodium methoxide was suspended in dry diethyl ether (300 ml), and methyl methylthioacetate (36 g) was added during 15 minutes to the stirred suspension, keeping the temperature below 5°. The mixture was stirred at 0° for 1 hour and methyl formate (20.4 ml) was added, keeping the temperature below 5°. The mixture was stirred overnight at ambient temperature and then extracted with water (2×150 ml) to give an aqueous solution of methyl 3-hydroxy-2-(methylthio)acrylate, sodium salt. This compound may also be isolated as a solid by filtration of the above ethereal reaction mixture.

(b) A mixture of methyl 3-aminothiophene-2-carboxylate (26.2 g) and aqueous sodium hydroxide (10%; 260 ml) was stirred and heated on a steam bath overnight to give an aqueous solution of sodium 3-aminothiophene-2-carboxylate. This solution was stirred, and treated with a portion (200 ml) of the above aqueous solution of methyl 3-hydroxy-2-(methylthio)acrylate, sodium salt below 5°. Concentrated hydrochloric acid (30 ml) was added dropwise to the stirred mixture, keeping the temperature at 0°–5°. The mixture was allowed to warm to room temperature over 1 hour and the resulting yellow solid was collected, washed with water and dried to give the novel compound 3-(2-methoxycarbonyl-2-methylthiovinylamino)thiophene-2-carboxylic acid. A portion was crystallised from industrial methylated spirit to give an analytical sample, m.p. 179°–180°.

(c) The above carboxylic acid (20.0 g) was added portionwise during 30 minutes to stirred diphenyl ether (200 ml) at 240°–250°. Stirring at this temperature was maintained for 30 minutes, methanol produced being distilled off. The mixture was cooled to ambient temperature and filtered. The solid product was washed with diethyl ether, dried and crystallised from industrial methylated spirit to give the novel compound 7-hydroxy-6-methylthiothieno[3,2-b]pyridine, m.p. 210°–212°.

(d) Dimethyl sulphate (2 ml) was added to a stirred solution of the above thieno[3,2-b]pyridine (1.97 g) and potassium hydroxide (1.68 g) in water (20 ml) at 0°–5°. The mixture was allowed to warm to ambient temperature and then kept at this temperature for 2 hours. The solid product was collected by filtration, dried and crystallised from ethyl acetate to give the novel compound 4-methyl-6-methylthiothieno[3,2-b]pyrid-7(4H)-one, m.p. 171°–174°.

EXAMPLE 2

A solution of 3-chloroperbenzoic acid (85%; 1.63 g) in dichloromethane (60 ml) was added dropwise during 20 minutes to a stirred solution of 4-methyl-6-methylthiothieno[3,2-b]pyrid-7(4H)-one (2.0 g) in dichloromethane (60 ml) at 0°–5°. After 4 hours, more 3-chloroperbenzoic acid (0.15 g) in dichloromethane (10 ml) was added and the mixture stirred overnight at ambient temperature. More 3-chloroperbenzoic acid (0.15 g) in dichloromethane (10 ml) was added and the mixture was again stirred overnight at ambient temperature. The resulting solution was extracted with saturated aqueous sodium bicarbonate solution (5×150 ml) and saturated aqueous sodium chloride solution (1×150 ml) and the organic phase was discarded. The aqueous extracts were combined and extracted with dichloromethane (5×100 ml). The organic extracts were combined, dried over anhydrous magnesium sulphate and evaporated to give a solid product. This product was crystallised from industrial methylated spirit to give the novel compound 4-methyl-6-methylsulphinylthieno[3,2-b]pyrid-7(4H)-one, m.p. 174°–176°. The infra-red spectrum was characteristic of Type 2 polymorphic form.

EXAMPLE 3

A solution of 3-chloroperbenzoic acid (85%; 5.7 g) in dichloromethane (130 ml) was added dropwise during 35 minutes to a stirred solution of 4-methyl-6-methylthiothieno[3,2-b]pyrid-7(4H)-one (2.9 g) in dichloromethane (200 ml). The mixture was stirred at ambient temperature for 5.5 hours. More 3-chloroperbenzoic acid (1.43 g) in dichloromethane (40 ml) was added and the mixture was stirred overnight at ambient temperature. The mixture was stirred with saturated aqueous sodium bicarbonate solution (180 ml) for 2 hours. The organic layer was separated and washed with further quantities of saturated aqueous sodium bicarbonate solution (3×200 ml), dried over anhydrous magnesium sulphate and evaporated. The resulting solid product was crystallised from industrial methylated spirit to give the novel compound 4-methyl-6-methylsulphonyl-thieno[3,2-b]pyrid-7(4H)-one, m.p. 258°–261°.

EXAMPLE 4

(a) Methanesulphonyl chloride (26.6 ml) and aqueous sodium hydroxide solution (1M, 36 ml) were added simultaneously to a stirred, ice-cooled solution of sodium sulphite heptahydrate (54.9 g) in water (325 ml) during 2 hours. The rate of addition of the sodium hydroxide solution was regulated to maintain the pH of the mixture between 6 and 8. When addition was complete, the mixture was allowed to warm to ambient temperature during 1 hour. To this aqueous solution of sodium methanesulphinate was added paraformaldehyde (19.3 g) and 7-hydroxythieno[3,2-b]pyridine (16.12 g) and the mixture was boiled under reflux for 24 hours. More paraformaldehyde (9.65 g) was added, the mixture was boiled under reflux for 20 hours, and then cooled to ambient temperature. The solid product was collected by filtration, washed with water and dried in vacuo to give the novel compound 7-hydroxy-6-methylsulphonylmethylthieno[3,2-b]pyridine, m.p. >300°.

(b) Dimethyl sulphate (17.4 g) was added to a stirred solution of the above thienopyridine (16.8 g) and potassium hydroxide (11.6 g) in water (210 ml) at 0°. The mixture was stirred at 0°–5° for 5 hours, then at room temperature overnight. The resulting precipitate was collected by filtration, washed with water, dried and crystallised twice from methanol to give the novel compound 4-methyl-6-methylsulphonylmethylthieno[3,2-b]pyrid-7(4H)-one, m.p. 220°–223°.

EXAMPLE 5

(a) A mixture of methyl 3-amino-5-methylthiophene-2-carboxylate (39 g) and sodium hydroxide (18 g) in water (300 ml) was stirred and heated on a steam bath for 16 hours to give an aqueous solution of sodium 3-amino-5-methylthiophene-2-carboxylate. This solution was stirred, cooled in ice, and treated dropwise during 70 minutes with a solution of methyl 3-hydroxy-2-(methylthio)acrylate, sodium salt (50 g) in water (300 ml). After 30 minutes, a mixture of dilute hydrochloric acid (5M, 160 ml) and water (300 ml) was added dropwise to the stirred mixture with cooling below 10°. The stirred mixture was allowed to warm to ambient temperature slowly and then filtered. The solid product was washed with water and dried to give the novel compound 3-(2-methoxycarbonyl-2-methylthiovinylamino)-5-methylthiophene-2-carboxylic acid, m.p. 153°–156°(dec).

(b) The above carboxylic acid (9 g) was added portionwise during 10 minutes to stirred diphenyl ether (300 ml) which was boiling under reflux in a nitrogen atmosphere. Stirring and boiling under reflux was continued for 22 minutes, the methanol produced being distilled off. The mixture was cooled to ambient temperature, diluted with diethyl ether, and filtered. The solid product was washed with diethyl ether and dried to give the novel compound 7-hydroxy-2-methyl-6-methylthiothieno[3,2-b]pyridine, m.p. 222°–225°.

(c) A mixture of the above thienopyridine (3 g), potassium carbonate (1.47 g) and dry dimethylformamide (45 ml) was stirred at ambient temperature for 10 minutes. Iodomethane (1.8 ml) was added to the mixture and stirring was continued for 70 hours. Ammonia (specific gravity 0.88; 0.15 ml) was added. After 3 hours the mixture was evaporated to dryness and the residue triturated with water (250 ml). The solid product was collected by filtration, washed with water and dried to give the novel compound 2,4-dimethyl-6-methylthiothieno[3,2-b]pyrid-7(4H)-one, m.p. 139°–141.5°.

EXAMPLE 6

In a similar way to that described in Example 2, 2,4-dimethyl-6-methylthiothieno[3,2-b]pyrid-7(4H)-one was oxidised with 3-chloroperbenzoic acid to give the novel compound 2,4-dimethyl-6-methylsulphinyl-thieno[3,2-b]pyrid-7(4H)-one, m.p. 263°–264°.

EXAMPLE 7

(a) In a similar way to that described in Example 5(c), 7-hydroxy-6-methylthiothieno[3,2-b]pyridine was butylated by reaction with iodobutane in the presence of potassium carbonate and dry dimethylformamide. There was obtained the novel compound 4-n-butyl-6-methylthiothieno[3,2-b]pyrid-7(4H)-one.

(b) In a similar way to that described in Example 2, the product from (a) was oxidised with 3-chloroperbenzoic acid to give the novel compound 4-n-butyl-6-methylsulphinylthieno[3,2-b]pyrid-7(4H)-one, m.p. 137°–138.5°.

EXAMPLE 8

(a) 4-Amino-2-phenylthiophene (1.0 g) was stirred with a mixture of hydrochloric acid (5N; 2.5 ml) and water (50 ml) at 40° for 1 hour. To this stirred suspension at ambient temperature was added a solution of methyl 3-hydroxy-2-(methylthio)acrylate, sodium salt (2 g) in water (50 ml) dropwise during 20 minutes. The mixture was stirred at 30° for 100 minutes, kept at ambient temperature for 18 hours, and filtered. The solid product was washed with water and dried to give the novel compound methyl (5-phenylthien-3-ylamino)acrylate, m.p. 108°–111°.

(b) The product from (a) (1.0 g) was added portionwise during 5 minutes to boiling diphenyl ether (50 ml) and boiling under reflux was continued for 40 minutes. The mixture was cooled and diethyl ether (65 ml) was added. The solid product was collected by filtration and dried to give the novel compound 7-hydroxy-6-methylthio-2-phenylthieno[3,2-b]pyridine, m.p. >325°.

(c) A mixture of the above thienopyridine (2.5 g), anhydrous potassium carbonate (1.3 g) and dry dimethylformamide (90 ml) was stirred at 20° for 15 minutes. Iodomethane (1.5 ml) was added to the stirred mixture and stirring was continued for 18 hours. The mixture was evaporated to dryness and the residue was triturated with water (100 ml). The solid product was collected by filtration, washed with water and dried to give the novel compound 4-methyl-6-methylthio-2-phenylthieno[3,2-b]pyrid-7(4H)-one, m.p. 225°-227° (dec.).

EXAMPLE 9

A solution of 3-chloroperbenzoic acid (85%; 1.69 g) in dichloromethane (50 ml) was added dropwise during 10 minutes to a stirred solution of 4-methyl-6-methylthio-2-phenylthieno[3,2-b]pyrid-7(4H)-one (2.25 g) in dichloromethane (500 ml) cooled in ice. The resulting solution was kept at 4° for 70 hours and evaporated to dryness at ambient temperature. The residue was triturated with diethyl ether (200 ml) to give a solid product. This product was purified by flash chromatography [described in J. Org. Chem., 43, 2923-5 (1978)] over a silica gel sold under the trade name Kieselgel 60 (particle size 0.040-0.063 mm) by E. Merck of Darmstadt, W. Germany using dichloromethane/methanol 95:5 as the eluent to give the novel compound 4-methyl-6-methylsulphinyl-2-phenylthieno[3,2-b]pyrid-7(4H)-one, m.p. 252°-255°.

EXAMPLE 10

(a) A solution of methyl 3-hydroxy-2-(methylthio)acrylate, sodium salt (10.2 g) in water (60 ml) was added to a stirred mixture of 3-amino-4-ethoxythiophene (6.3 g), concentrated hydrochloric acid (3.7 ml) and water (50 ml) at 0°-5° during 15 minutes. The mixture was stirred at ambient temperature for 20 hours and the solid product was collected by filtration to give the novel compound methyl 3-(4-ethoxythien-3-ylamino)-2-(methylthio)acrylate.

(b) A solution of the product from (a) in diphenyl ether (150 ml) was added during 15 minutes to stirred diphenyl ether (500 ml) at 250°-260°. Stirring at this temperature was continued for 30 minutes and the mixture was then cooled to ambient temperature. The mixture was diluted with diethyl ether (1200 ml). The resulting solid product was collected by filtration, washed with boiling diethyl ether and dried to give the novel compound 3-ethoxy-7-hydroxy-6-methylthiothieno[3,2-b]pyridine, m.p. 180°-183°.

(c) A mixture of the above thienopyridine (1.46 g), iodomethane (1.08 ml), anhydrous potassium carbonate (1.08 g) and dry dimethylformamide (30 ml) was stirred at ambient temperature for 48 hours. Aqueous ammonia (specific gravity 0.88; 2 ml) was added. The mixture was stirred for 30 minutes and then evaporated to dryness. The residue was washed with water (30 ml) and crystallised from industrial methylated spirit to give the novel compound 3-ethoxy-4-methyl-6-methylthiothieno[3,2-b]pyrid-7(4H)-one, m.p. 214°-217°.

EXAMPLE 11

A solution of 3-chloroperbenzoic acid (85%; 0.55 g) in dichloromethane (25 ml) was added dropwise during 2 minutes to a stirred solution of 3-ethoxy-4-methyl-6-methylthiothieno[3,2-b]pyrid-7(4H)-one (0.7 g) in dichloromethane (50 ml) at 0°-5°. Stirring was continued at 0°-5° for 30 minutes. The mixture was washed with saturated aqueous sodium bicarbonate solution (20 ml) at ambient temperature. The aqueous phase was separated and extracted with dichloromethane (2×30 ml). The organic phases were combined, dried and evaporated to give a residue which was crystallised from industrial methylated spirit to give the novel compound 3-ethoxy-4-methyl-6-methylsulphinylthieno[3,2-b]pyrid-7(4H)-one, m.p. 210°-214°.

EXAMPLE 12

(a) Phosphoryl chloride (185 ml) was added during 20 minutes to dimethylformamide (310 ml) with stirring and ice cooling to maintain the temperature below 25°. The resulting solution was stirred at ambient temperature for 20 minutes and was then treated dropwise during 25 minutes with 2'-chloroacetophenone (120 ml), maintaining the temperature at 30°. The mixture was warmed to 50° and hydroxylamine hydrochloride (280 g) was added portionwise during 1 hour, causing a violent exothermic reaction with effervescence. The stirred mixture was cooled to room temperature during 30 minutes, water (2 liters) was added and stirring continued for 2 hours. The organic phase was separated and fractionally distilled under reduced pressure to give 3,2'-dichlorocinnamonitrile as a pale yellow liquid, b.p. 190°-200°/0.1 mmHg.

(b) A solution of methyl mercaptoacetate (53.8 g) in methanol (75 ml) was added during 15 minutes to a stirred solution of sodium methoxide (27.3 g) in methanol (590 ml). A solution of the nitrile from (a) (98 g) in methanol (1.5 liters) was added. The solution was boiled under reflux for 10 minutes, then cooled and poured into ice/water (5 liters). After 1 hour the solid product was collected by filtration, washed with water and dried to give the novel compound methyl 3-amino-5-(2-chlorophenyl)thiophene-2-carboxylate. An analytical sample crystallised from light petroleum, b.p. 40°-60°/dichloromethane 1:1 had m.p. 104°-105°.

(c) In a similar manner to that described in Example 5(a) the above carboxylate ester was converted to the corresponding carboxylic acid, sodium salt which was reacted with methyl 3-hydroxy-2-(methylthio)acrylate, sodium salt to give the novel compound 5-(2-chlorophenyl)-3-(2-methoxycarbonyl-2-methylthiovinylamino)thiophene-2-carboxylic acid, m.p. 80°-85°.

(d) In a similar manner to that described in Example 5(b), the above carboxylic acid was cyclised in boiling diphenyl ether to give the novel compound 2-(2-chlorophenyl)-7-hydroxy-6-methylthiothieno[3,2-b]pyridine, m.p. 270°-273°.

(e) In a similar manner to that described in Example 5(c), the above thienopyridine was methylated by reaction with iodomethane to give the novel compound 2-(2-chlorophenyl)-4-methyl-6-methylthiothieno[3,2-b]pyrid-7(4H)-one, m.p. 175°-177° (from industrial methylated spirit).

EXAMPLE 13

In a similar manner to that described in Example 11, 2-(2-chlorophenyl)-4-methyl-6-methylthiothieno[3,2- b]pyrid-7(4H)-one was oxidised with 3-chloroperbenzoic acid to give the novel compound 2-(2-chlorophenyl)-4-methyl-6-methylsulphinylthieno[3,2-b]pyrid-7(4H)-one, m.p. 167°–169° (from dichloromethane).

EXAMPLE 14

(a) In a similar manner to that described in Example 12(a), 3′-chloroacetophenone was converted to 3,3′-dichlorocinnamonitrile, which was isolated as a brown solid and used in the next stage without purification.

(b) In a similar manner to that described in Example 12(b), the above nitrile was converted to the novel compound methyl 3-amino-5-(3-chlorophenyl)thiophene-2-carboxylate.

(c) In a similar manner to that described in Example 5(a), the above carboxylate ester was converted to the corresponding carboxylic acid, sodium salt, which was reacted with methyl 3-hydroxy-2-(methylthio)acrylate, sodium salt to give the novel compound 5-(3-chlorophenyl)-3-(2-methoxycarbonyl-2-methylthiovinylamino)thiophene-2-carboxylic acid, m.p. 84°–86°.

(d) In a similar manner to that described in Example 5(b), the above carboxylic acid was cyclised in boiling diphenyl ether to give the novel compound 2-(3-chlorophenyl)-7-hydroxy-6-methylthiothieno[3,2-b]pyridine, m.p. >300°.

(e) In a similar manner to that described in Example 5(c), the above thienopyridine was methylated by reaction with iodomethane to give the novel compound 2-(3-chlorophenyl)-4-methyl-6-methylthiothieno[3,2-b]pyrid-7(4H)-one, m.p. 234°–236° (from industrial methylated spirit).

EXAMPLE 15

In a similar manner to that described in Example 11, 2-(3-chlorophenyl)-4-methyl-6-methylthiothieno[3,2-b]pyrid-7(4H)-one was oxidised with 3-chloroperbenzoic acid to give the novel compound 2-(3-chlorophenyl)-4-methyl-6-methylsulphinylthieno[3,2-b]pyrid-7(4H)-one, m.p. 249°–251° (from industrial methylated spirit).

EXAMPLE 16

(a) In a similar manner to that described in Example 5(a), methyl 3-amino-5-(4-methoxyphenyl)thiophene-2-carboxylate was converted to the corresponding carboxylic acid, sodium salt, which was reacted with methyl 3-hydroxy-2-(methylthio)acrylate, sodium salt to give the novel compound 3-(2-methoxycarbonyl-2-methylthiovinylamino)-5-(4-methoxyphenyl)thiophene-2-carboxylic acid as a solid product.

(b) In a similar manner to that described in Example 5(b), the above carboxylic acid was cyclised in boiling diphenyl ether to give the novel compound 7-hydroxy-2-(4-methoxyphenyl)-6-methylthiothieno[3,2-b]pyridine, m.p. 283°–287°.

(c) In a similar manner to that described in Example 5(c), the above thienopyridine was methylated with iodomethane. The product was purified by flash chromatography over Kieselgel 60 using dichloromethane/industrial methylated spirit 95:5 as the eluent, followed by a recrystallisation from industrial methylated spirit. There was obtained the novel compound 2-(4-methoxyphenyl)-4-methyl-6-methylthiothieno[3,2-b]pyrid-7(4H)-one, m.p. 182°–184°.

(d) In a similar manner to that described in Example 11, the above sulphide was oxidised with 3-chloroperbenzoic acid. The product was purified by flash chromatography over Kieselgel 60 using dichloromethane/industrial methylated spirit 98:2 as the eluent. There was obtained the novel compound 2-(4-methoxyphenyl)-4-methyl-6-methylsulphinylthieno[3,2-b]pyrid-7(4H)-one, m.p. 262°–264°.

EXAMPLE 17

(a) A solution of methyl mercaptoacetate (11 ml) in methanol (50 ml) was added dropwise during 15 minutes to a stirred solution of sodium methoxide in methanol (27.9% w/v; 23 g) cooled in ice. After 25 minutes a solution of 3-chloro-2-phenylacrylonitrile (20 g) in methanol (80 ml) was added dropwise during 30 minutes to the stirred, cooled mixture. The mixture was allowed to warm to 20° and a solution of sodium methoxide in methanol (27.9% w/v; 23 g) was added. After 18 hours the solid product was collected by filtration, washed with water and dried to give the novel compound methyl 3-amino-4-phenylthiophene-2-carboxylate, m.p. 64°–66°.

(b) In a similar manner to that described in Example 5(a), the above carboxylate ester was converted to the corresponding carboxylic acid, sodium salt, which was reacted with methyl 3-hydroxy-2-(methylthio)acrylate, sodium salt to give the novel compound 3-(2-methoxycarbonyl-2-methylthiovinylamino)-4-phenylthiophene-2-carboxylic acid, m.p. 90°–92°.

(c) In a similar manner to that described in Example 5(b), the above carboxylic acid was cyclised in boiling diphenyl ether to give the novel compound 7-hydroxy-6-methylthio-3-phenylthieno[3,2-b]pyridine, m.p. 273°–275°.

(d) In a similar manner to that described in Example 5(c), the above thienopyridine was methylated with iodomethane to give a crude product. Purification by flash chromatography over Kieselgel 60 using dichloromethane/industrial methylated spirit 98.5:1.5 as the eluent gave a pure sample of the novel compound 4-methyl-6-methylthio-3-phenylthieno[3,2-b]pyrid-7(4H)-one, m.p. 204°–206° and a less pure sample of the same compound.

(e) In a similar way to that described in Example 11, the above less pure sample of sulphide was oxidised with 3-chloroperbenzoic acid. The product was purified by flash chromatography over Kieselgel 60 using dichloromethane/industrial methylated spirit 97:3 as the eluent to give the novel compound 4-methyl-6-methylsulphinyl-3-phenylthieno[3,2-b]pyrid-7(4H)-one, m.p. 206°–209°.

EXAMPLE 18

(a) A solution of triethylamine (34.8 ml) in dioxan (25 ml) was added during 30 minutes to a stirred mixture of mercaptoacetic acid (13.9 ml), tiglic acid (20.0 g) and dioxan (25 ml) at 90°–95°. The mixture was stirred at 95° for 5 hours, cooled, poured on to ice (300 g), acidified with concentrated hydrochloric acid to pH 3 and extracted with diethyl ether (3×100 ml). The extract was dried and evaporated to give 3-(carboxymethylthio)-2-methylbutanoic acid as an oil.

(b) All the above dicarboxylic acid was added to a mixture of lithium acetate (1.0 g) and acetic anhydride (150 ml) and the mixture was stirred at 170° until evolution of carbon dioxide ceased. The mixture was cooled, poured onto a mixture of ice (400 g) and concentrated sulphuric acid (5 ml), stirred for 2 hours and extracted with diethyl ether (3×200 ml). The extract was washed with saturated aqueous sodium bicarbonate, dried and evaporated to give an oil. This oil was distilled under reduced pressure to give 2,3-dimethyl-4-oxo-2,3,4,5-tetrahydrothiophene, b.p. 91°-93°/20 mmHg.

(c) A mixture of the above ketone (7.18 g), ethanol (180 ml), hydroxylamine hydrochloride (7.2 g) and barium carbonate (14.4 g) was stirred and boiled under reflux for 53 hours, then filtered while hot. The filtrate was evaporated to give an oil which was dissolved in diethyl ether (400 ml). Saturated ethanolic hydrogen chloride (100 ml) was added, the mixture was kept at ambient temperature for 3 days and then evaporated. The resulting oil was triturated with ether to give a solid which was collected by filtration, washed with diethyl ether and dried to give 2,3-dimethyl-4-aminothiophene hydrochloride, m.p. 189°-193° (dec.)

(d) An aqueous solution of methyl 3-hydroxy-2-(methylthio)acrylate, sodium salt (14.4% ; 220 ml) was added to a stirred mixture of the above amine hydrochloride (27.0 g) and water (200 ml) at 0°-5°. The mixture was stirred at ambient temperature for 22 hours. The aqueous phase was separated off leaving the novel compound methyl 3-(4,5-dimethylthien-3-ylamino)-2-(methylthio)acrylate as an oil.

(e) A solution of the above oil in diphenyl ether (200 ml) was added during 15 minutes with stirring under nitrogen to diphenyl ether (450 ml) at 250°-255°. The mixture was stirred at this temperature for 20 minutes, then cooled to ambient temperature and diluted with diethyl ether (450 ml). The solid product was collected by filtration, washed with diethyl ether and dried to give the novel compound 7-hydroxy-2,3-dimethyl-6-methylthiothieno[3,2-b]pyridine, m.p. 233°-236°.

(f) In a similar way to that described in Example 5(c), the above thienopyridine was methylated with iodomethane to give the novel compound 2,3,4-trimethyl-6-methylthiothieno[3,2-b]pyrid-7(4H)-one, m.p. 225°-230° (crystallised from industrial methylated spirit, recrystallised from methanol).

(g) In a similar manner to that described in Example 11, the product from (f) was oxidised with 3-chloroperbenzoic acid to give the novel compound 2,3,4-trimethyl-6-methylsulphinylthieno[3,2-b]pyrid-7(4H)-one, m.p. 253°-258° (dec.) (from industrial methylated spirit).

EXAMPLE 19

(a) Ethanol (26.4 ml) was added dropwise during 7 minutes to a stirred mixture of phosphorus pentoxide and xylene (45 ml) cooled in ice. The stirred mixture was then heated to 65°-70° and 3-(2-methoxycarbonyl-2-methylthiovinylamino)thiophene-2-carboxylic acid (16.38 g) added portionwise during 5 minutes. The stirred mixture was heated at 120° for 70 minutes, allowed to cool to 70°, and poured into water (70 ml). The solid product was collected by filtration, washed with water, dried and crystallised from industrial methylated spirit to give the novel compound 7-hydroxy-6-methylthiothieno[3,4-b]pyridine, m.p. 289°-293°.

(b) The above thienopyridine was methylated with iodomethane in a similar manner to that described in Example 5(c). There was obtained the novel compound 4-methyl-6-methylthiothieno[3,4-b]pyrid-7(4H)-one, m.p. 142°-145°.

EXAMPLE 20

In a similar manner to that described in Example 11, 4-methyl-6-methylthiothieno[3,4-b]pyrid-7(4H)-one was oxidised with 3-chloroperbenzoic acid to give the novel compound 4-methyl-6-methylsulphinylthieno[3,4-b]pyrid-7(4H)-one, m.p. 205° (sublimation) (from industrial methylated spirit).

EXAMPLE 21

(a) In a similar manner to that described in Example 1(b), methyl 2-aminothiophene-3-carboxylate was converted to the corresponding carboxylic acid which was reacted with methyl 3-hydroxy-2-(methylthio)acrylate, sodium salt. The product was isolated by extraction with dichloromethane. There was obtained the novel compound 2-(2-methoxycarbonyl-2-methylthiovinylamino)thiophene-3-carboxylic acid, m.p. 192°-194°) (from isopropanol).

(b) In a similar manner to that described in Example 5(b), the above carboxylic acid was cyclised in diphenyl ether at 255°. There was obtained the novel compound 4-hydroxy-5-methylthiothieno[2,3-b]pyridine, m.p. 203°-205°.

(c) A mixture of the above thienopyridine (3.9 g), dimethyl sulphate (2.0 ml), anhydrous potassium carbonate (3.0 g) and dry butanone (200 ml) was stirred and boiled under reflux for 2 hours. The mixture was evaporated to dryness. Water (200 ml) was added and the mixture was basified with aqueous potassium hydroxide (5N). The mixture was stirred for 2 hours and then extracted with dichloromethane (3×100 ml). The combined extracts were dried, evaporated to a small volume and diluted with light petroleum (b.p. 40°-60°). The resulting solid product was collected by filtration, washed with light petroleum (b.p. 40°-60°) and dried to give the novel compound 7-methyl-5-methylthiothieno[2,3-b]pyrid-4(7H)-one, m.p. 138°-140°.

EXAMPLE 22

In a similar way to that described in Example 11, 7-methyl-5-methylthiothieno[2,3-b]pyrid-4(7H)-one was oxidised with 3-chloroperbenzoic acid at −10°. The product was purified by column chromatography over silica gel using dichloromethane/industrial methylated spirit 9:1 as the eluent to give the novel compound 7-methyl-5-methylsulphinylthieno[2,3-b]pyrid-4(7H)-one, m.p. 150°-152°.

EXAMPLE 23

(a) Iron powder (reduced, 57 g) was added to a stirred mixture of methyl 3-acetamido-5-nitrothiophene-2-carboxylate (29.0 g) and ammonium chloride (7.5 g) in water (400 ml) at 95°. The mixture was stirred at 95° for 3.5 hours and then filtered while hot through kieselguhr to give filtrate (A). The solid was washed with hot water and the wash liquid kept separate from the filtrate (A). A solid which separated from the wash liquid was collected by filtration and dried to give methyl 3-acetamido-5-aminothiophene-2-carboxylate, m.p. 162°-163°. Further product was obtained by extraction of the filtrate (A) with ethyl acetate.

(b) A solution of sodium nitrite (18.0 g) in water (54 ml) was added dropwise to a stirred solution of the product from (a) (18.0 g) in dilute sulphuric acid (5N, 500 ml) at −10°. After stirring the mixture for 20 minutes at −5°, concentrated hydrochloric acid (360 ml) was added. The mixture was allowed to warm slowly from 0° to ambient temperature. After 70 hours the mixture was extracted with dichloromethane (3×500 ml). The extract was dried and evaporated to give the novel compound N-(5-diazonio-2-methoxycarbonyl-3-thienyl)amide.

(c) A solution of the above diazonio compound (1.5 g) in concentrated hydrochloric acid (40 ml) at 25° was added portionwise during 5 minutes to a stirred solution of cuprous chloride (3.1 g) in concentrated hydrochloric acid (10 ml) initially at −10°. The stirred mixture was allowed to warm slowly to ambient temperature. After 3 hours the mixture was heated on a steam bath for 10 minutes, then cooled in an ice/salt mixture. The solid product was collected by filtration and crystallised from industrial methylated spirit to give the novel compound methyl 3-amino-5-chlorothiophene-2-carboxylate.

(d) In a similar manner to that described in Example 5(a), the above carboxylate ester was converted to the novel compound methyl 3-(5-chlorothien-3-ylamino)-2-(methylthio)acrylate mixed with 5-chloro-3-(2-methoxycarbonyl-2-methylthiovinylamino)thiophene-2-carboxylic acid.

(e) In a similar manner to that described in Example 5(b), the above mixture of thiophene compounds (0.5 g) was cyclised in boiling diphenyl ether to give the novel compound 2-chloro-7-hydroxy-6-methylthiothieno[3,2-b]pyridine, m.p. 235°-237°.

(f) In a similar manner to that described in Example 5(c), the above thienopyridine was methylated with iodomethane to give the novel compound 2-chloro-4-methyl-6-methylthiothieno[3,2-b]pyrid-7(4H)-one, m.p. 231°-234°.

(g) In a similar manner to that described in Example 11, the product from (f) was oxidised with 3-chloroperbenzoic acid at −5° to 0° to give the novel compound 2-chloro-4-methyl-6-methylsulpinylthieno[3,2-b]pyrid-7(4H)-one, m.p. 245°-247° (from industrial methylated spirit).

EXAMPLE 24

(a) A solution of 3-chloroperbenzoic acid (85%; 13.9 g) in dichloromethane (400 ml) was added dropwise during 7 hours to a stirred suspension of 7-hydroxy-6-methylthiothieno[3,2-b]pyridine (15 g) in dichloromethane (500 ml) at 0°-5°. Further oxidation with more 3-chloroperbenzoic acid (two portions of 1.5 g) was carried out until the reaction was complete as shown by thin layer chromatography. A solution of sodium sulphite (6 g) in water (20 ml) was added to destroy any remaining peroxides. The mixture was evaporated to dryness and the residue was triturated with diethyl ether. The solid product was recrystallised from water and purified by high pressure liquid chromatography over silica using dichloromethane/industrial methylated spirit 90:10 as the eluent to give the novel compound 7-hydroxy-6-methylsulphinylthieno[3,2-b]pyridine, m.p. 271°-273°.

(b) Dimethyl sulphate (3.85 g) was added dropwise to a solution of the above thienopyridine (3.0 g) and potassium hydroxide (2.5 g) in water (31.7 ml) at 0°-5°. The mixture was allowed to warm to ambient temperature and was stirred at ambient temperature for 4 hours. The resulting precipitate was collected and crystallised from industrial methylated spirit to give the novel compound 4-methyl-6-methylsulphinylthieno[3,2-b]pyrid-7(4H)-one, m.p. 199°. The infra-red spectrum was characteristic of Type 1 polymorphic form.

EXAMPLE 25

(a) In a similar manner to that described in Example 23(c), N-(5-diazonio-2-methoxycarbonyl-3-thienyl)amide (0.4 g) in hydrobromic acid (48% w/v; 5 ml) was reacted with a solution of cuprous bromide (1 g) in hydrobromic acid (48% w/v; 5 ml) to give the novel compound methyl 3-amino-5-bromothiophene-2-carboxylate, m.p. 173°-176°.

(b) In a similar manner to that described in Example 5(a), the above carboxylate ester was converted to the novel compound methyl 3-(5-bromothien-3-ylamino)-2-(methylthio)acrylate mixed with 5-bromo-3-(2-methoxycarbonyl-2-methylthiovinylamino)thiophene-2-caboxylic acid.

(c) In a similar manner to that described in Example 5(b), the above mixture of thiophene compounds (4.5 g) was cyclised in boiling diphenyl ether to give the novel compound 2-bromo-7-hydroxy-6-methylthiothieno[3,2-b]pyridine, m.p. 278° (dec).

(d) In a similar manner to that described in Example 5(c), the above thienopyridine was methylated with iodomethane to give the novel compound 2-bromo-4-methyl-6-methylthiothieno[3,2-b]pyrid-7(4H)-one, m.p. 204° (dec).

(e) A mixture of the above thienopyridone (2.35 g), cuprous iodide (0.77 g), methanolic sodium methoxide (4.3 ml of 30% w/v solution plus 2.7 ml methanol) and pyridine (27 ml) was boiled and stirred under reflux in an atmosphere of argon for 140 minutes. The solvent was distilled off under reduced pressure and the residue was extracted with dichloromethane for 6 hours using a Soxhlet apparatus. The extract was exaporated to dryness to give a solid product which was purified by high performance liquid chromatography over silica gel using dichloromethane/heptane/isopropanol 60:35:5 as the eluent. There was obtained the novel compound 2-methoxy-4-methyl-6-methylthiothieno[3,2-b]pyrid-7(4H)-one, m.p. 185°-187°.

EXAMPLE 26

In a similar manner to that described in Example 11, 2-methoxy-4-methyl-6-methylthiothieno[3,2-b]pyrid-7(4H)-one was oxidised with 3-chloroperbenzoic acid. The product was purified by preparative layer chromatography over silica using dicholoromethane/industrial methylated spirit 19:1 as the eluent. There was obtained the novel compound 2-methoxy-4-methyl-6-methylsulphinylthieno[3,2-b]pyrid-7(4H)-one, m.p. 244°-247° (dec.).

EXAMPLE 27

(a) A mixture of methyl 3-aminothiophene-2-carboxylate (20 g), triethyl orthoformate (70 ml) and trifluoroacetic acid (9 drops) was stirred and heated at 180° for 5.75 hours, the ethanol formed being removed by distillation. The resulting mixture was evaporated to dryness. Absolute ethanol (60 ml) was added to the residue and the mixture cooled to 0°. Sodium borohydride (6.1 g) was added portionwise with stirring and the mixture was allowed to warm to ambient temperature. An exothermic reaction occurred and cooling was applied to control the rise in temperature. After the exothermic reaction had subsided the mixture was heated on a steam bath for 3 hours, cooled, and poured into ice-water. The resulting oil was extracted with dichloromethane. the extract was washed with water, dried and evaporated to give an oily residue which was crystallised from light petroleum (b.p. 60°-80°) to give the novel compound methyl 3-methylaminothiophene-2-carboxylate, m.p. 54°-57°.

(b) A mixture of dry dimethyl sulphoxide (70 ml), dry toluene (180 ml) and sodium hydride (50% dispersion in oil; 7.7 g) was stirred and heated at 65°-70° under nitrogen for 1.75 hours. The mixture was cooled in ice-water and the above carboxylate ester (5.2 g) added portionwise below 45° during 15 minutes. The mixture was heated at 40°-45° for 30 minutes, cooled and poured into diethyl ether (700 ml). The solid precipitate was collected, dissolved in the minimum amount of water and the solution was acidified to pH 6 with acetic acid. After a few minutes the solution was saturated with potassium carbonate and extracted with ethyl acetate. The organic extract was dried and evaporated to dryness. The residue way crystallised from diethyl ether/ethanol 3:1 to give the novel compound 1-(3-methylaminothien-2-yl)-2-(methylsulphinyl)-ethanone, m.p. 125°-127°.

(c) A mixture of the above ethanone (1.6 g), triethyl orthoformate (13 ml), absolute ethanol (13 ml) and glacial acetic acid (0.7 ml) was stirred and boiled under reflux in an atmosphere of nitrogen until the reaction was complete as indicated by thin-layer chromatography (reaction time 24 hours). The mixture was evaporated to dryness to give an oil which partly solidified on standing. The product was crystallised from methanol to give 4-methyl-6-methylsulphinylthieno[3,2-b]pyrid-7(4H)-one, m.p. 173°.

EXAMPLE 28

A solution of 4-methyl-6-methylsulphinylthieno-[3,2-b]pyrid-7(4H)-one (1 g) in absolute ethanol (70 ml) was added to a solution of fumaric acid (0.5 g) in absolute ethanol (20 ml) and the mixture was kept at 0°-5° overnight. The resulting precipitate was collected and dried to give the novel compound 4-methyl-6-methylsulphinylthieno[3,2-b]pyrid-7(4H)-one 0.45 fumarate, m.p. 205°-206°.

EXAMPLE 29

A solution of 4-methyl-6-methylsulphinylthieno[3,2-b]pyrid-7(4H)-one (1 g) in absolute ethanol (70 ml) was treated with hydrogen chloride gas, the temperture of the mixture being maintained at about 20° by means of ice cooling. A white solid precipitated and treatment with hydrogen chloride was continued until precipitation ceased. The mixture was left at ambient temperature overnight, and the solid product was collected by filtration and dried to give the novel compound 4-methyl-6-methylsulphinylthieno[3,2-b]pyrid-7(4H)-one hydrochloride in crude form. On standing, a second crop of pure product separated from the filtrate which was collected and dried to give the pure hydrochloride, m.p. 147°-153° (dec).

EXAMPLE 30

In the preparation of capsules, 100 parts by weight of active compound and 250 parts by weight of lactose are de-aggregated and blended. The mixture is filled into hard gelatin capsules, each capsule containing 100 mg of active compound.

EXAMPLE 31

Tablets are prepared from the following ingredients.

| | parts by weight |
|---|---|
| Active compound | 100 |
| Lactose | 100 |
| Maize starch | 22 |

-continued

| | parts by weight |
|---|---|
| Polyvinylpyrrolidone | 10 |
| Magnesium stearate | 3 |

The active compound, the lactose and some of the starch are de-aggregated, blended and the resulting mixture is granulated with a solution of the polyvinylpyrrolidone in ethanol. The dry granulate is blended with the magnesium stearate and the rest of the starch. The mixture is then compressed in a tableting machine to give tablets containing 100 mg active compound.

EXAMPLE 32

Tablets are prepared by the method of Example 31. The tablets are enteric coated in a conventional manner using a solution of 20% cellulose acetate phthalate and 3% diethyl phthalate in ethanol:dichloromethane 1:1.

EXAMPLE 33

In the preparation of suppositories, 100 parts by weight of active compound is incorporated in 1300 parts by weight of tri-glyceride suppository base and the mixture formed into suppositories each containing 100 mg of active compound.

We claim:

1. A thienopyridone of the formula V,

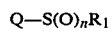

or a pharmaceutically acceptable acid addition salt thereof, wherein n is 0 or 1, $R_1$ is lower alkyl, and Q is a group of the formula VA or VB,

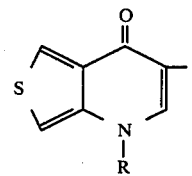

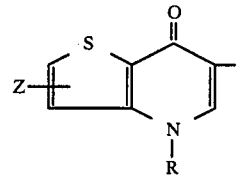

wherein R is lower alkyl and Z in formula VB is hydrogen, lower alkoxy, 2-(lower alkyl), 2-phenyl, 2-(2-halophenyl) or 2-(3-halophenyl).

2. A thienopyridone according to claim 1 of the formula VD,

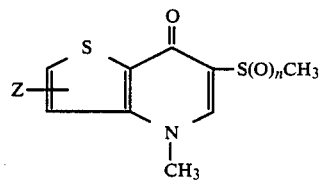

wherein n is 0 or 1 and Z is as defined in claim 1.

3. a thienopyridone according to claim 2 wherein Z is hydrogen, methoxy, ethoxy, 2-methyl, 2-phenyl, 2-(2-chlorophenyl) or 2-(3-chlorophenyl) and n is 1.

4. The compound according to claim 1, which is 4-methyl-6-methylsulphinylthieno[3,2-b]pyrid-7(4H)-one.

5. The compound according to claim 1, which is 4-methyl-6-methylthio-2-phenylthieno[3,2-b]-pyrid-7(4H)-one.

6. The compound according to claim 1, which is 4-methyl-6-methylsulphinyl-2-phenylthieno[3,2-b]-pyrid-7(4H)-one.

7. A thienopyridone of the formula VC,

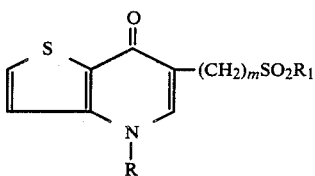
VC wherein m is 0 or 1, R is lower alkyl and R₁ is lower alkyl.

8. A thienopyridone according to claim 7 wherein R and R₁ are methyl.

9. The compound according to claim 7, which is 4-methyl-6-methylsulphonylthieno[3,2-b]pyrid-7(4H)-one.

10. A pharmaceutical composition useful for treating hypertension or heart failure in humans, which comprises an effective amount of a thienopyridone of the formula V, $$Q-S(O)_nR_1 \quad \quad V$$

wherein n is 0 or 1, R₁ is lower alkyl, and Q is a group of the formula VA or VB,

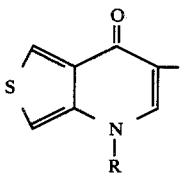
VA

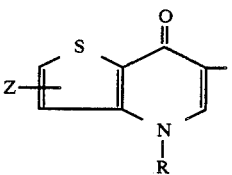
VB wherein R is lower alkyl and Z in formula VB is hydrogen, lower alkoxy, 2-(lower alkyl), 2-phenyl, 2-2(-halophenyl) or 2-(3-halophenyl), in combination with a pharmaceutically acceptable carrier.

11. A pharmaceutical coposition useful for treating hypertension or heart failure in humans, which comprises an effective amount of a thienopyridone of the formula VD,

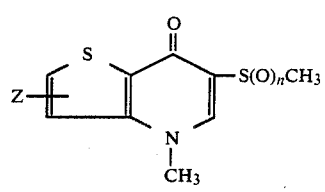
VD wherein n is 0 or 1 and Z is hydrogen, lower alkoxy, 2-(lower alkyl), 2-phenyl, 2-(2-halophenyl) or 2-(3-halophenyl), in combination with a pharmaceutically acceptable carrier.

12. A pharmaceutical composition according to claim 15 wherein Z is hydrogen, methoxy, ethoxy, 2-methyl, 2-phenyl, 2-(2-chlorophenyl) or 2-(3-chlorophenyl) and n is 1.

13. A pharmaceutical composition according to claim 11 wherein the thienopyridone is 4-methyl-6-methylsulphinylthieno[3,2-b]pyrid-7(4H)-one.

14. A pharmaceutical composition according to claim 10, wherein the thienopyridone is 4-methyl-6-methylthio-2-phenylthieno[3,2-b]pyrid-7(4H) one.

15. A pharmaceutical composition according to claim 10, wherein the thienopyridone is 4-methyl-6-methylsulphinyl-2-phenylthieno-[3,2-b]-pyrid-7(4H)-one.

16. A pharmaceutical composition useful for treating hypertension or heart failure in humans, which comprises an effective amount of a thienopyridone of the formula VC,

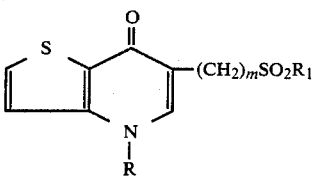
VC wherein m is 0 or 1, R is lower alkyl and R₁ is lower alkyl, in combination with a pharmaceutically acceptable carrier.

17. A pharmaceutical composition according to claim 16 wherein R and R₁ are methyl.

18. A pharmaceutical composition according to claim 11 wherein the thienopyridone is 4-methyl-6-methylsulphonylthieno[3,2-b]pyrid-7(4H)-one.

19. A method of treating hypertension in humans, which comprises administering to a human in need thereof a therapeutically effective amount of the compound of claim 4.

20. A method of treating hypertension in humans, which coprises administering to a human in need thereof a therapeutically effective amount of the compound of claim 2.

21. A method of treating hypertension in humans, which comprises administering to a human in need thereof a therapeutically effective amount of the compound of claim 3.

22. A method of treating hypertension in humans, which comprises administering to a human in need thereof a therapeutically effective amount of the compound of claim 7.

23. A method of treating hypertension in humans, which comprises administering to a human in need thereof a therapeutically effective amount of the compound of claim 8.

24. A method of treating hypertension in humans, which comprises administering to a human in need thereof a therapeutically effective amount of the compound of claim 4.

25. A method of treating hypertension in humans, which comprises administering to a human in need thereof a therapeutically effective amount of the compound of claim 9.

26. A method of treating heart failure in humans, whcih comprises administering to a human in need thereof a therapeutically effective amount of a compound according to claim 1.

27. A method of treating heart failure in humans, which comprises administering to a human in need thereof a therapeutically effective amount of a compound according to claim 2.

28. A method of treating heart failure in humans, which comprises administering to a human in need thereof a therapeutically effective amount of a compound according to claim 3.

29. A method of treating heart failure in humans, which comprises administering to a human in need thereof a therapeutically effective amount of a compound according to claim 7.

30. A method of treating heart failure in humans, which comprises administering to a human in need thereof a therapeutically effective amount of a compound according to claim 8.

31. A method of treating heart failure in humans, which comprises administering to a human in need thereof a therapeutically effective amount of a compound according to claim 4.

32. A method of treating heart failure in humans, which comprises administering to a human in need thereof a therapeutically effective amount of a compound according to claim 9.

33. A method of treating hypertension in humans, which comprises administering to a human in need thereof a therapeutically effective amount of the compound of claim 5.

34. A method of treating hypertension in humans, which comprises administering to a human in need thereof a therapeutically effective amount of the compound of claim 6.

35. A method of treating heart failure in humans, which comprises administering to a human in need thereof a therapeutically effective amount of a compound according to claim 5.

36. A method of treating heart failure in humans, which comprises administering to a human in need thereof a therapeutically effective amount of a compound according to claim 6.

* * * * *

UNITED STATES PATENT AND TRADEMARK OFFICE
CERTIFICATE OF CORRECTION

PATENT NO. : 4,710,506

DATED : December 1, 1987

INVENTOR(S) : Roy V. Davies et al

It is certified that error appears in the above-identified patent and that said Letters Patent are hereby corrected as shown below:

Column 23, claim 3, line 1, change "a" to --A--.
Column 24, claim 12, line 2, change "15" to --11--.
Claim 13, line 2, change "11" to --10--.
Claim 18, line 2, change "11" to --16--.
Claim 19, line 4, change "4" to --1--.

Signed and Sealed this

Second Day of August, 1988

Attest:

DONALD J. QUIGG

Attesting Officer     Commissioner of Patents and Trademarks